(12) United States Patent
Saebo et al.

(10) Patent No.: US 6,891,054 B2
(45) Date of Patent: May 10, 2005

(54) FUNCTIONAL ACYLGLYCERIDES

(75) Inventors: Asgeir Saebo, Oersta (NO); Jo Klaveness, Oslo (NO)

(73) Assignee: Natural AS (NO)

( * ) Notice: Subject to any disclaimer, the term of this patent is extended or adjusted under 35 U.S.C. 154(b) by 0 days.

(21) Appl. No.: 10/724,956

(22) Filed: Dec. 1, 2003

(65) Prior Publication Data

US 2004/0122094 A1 Jun. 24, 2004

Related U.S. Application Data

(63) Continuation of application No. 09/989,835, filed on Nov. 20, 2001, now Pat. No. 6,677,470.

(51) Int. Cl.$^7$ ............................................. C07C 57/00
(52) U.S. Cl. ........................ 554/227; 514/547; 426/601
(58) Field of Search ...................... 554/227; 514/547; 426/601

(56) References Cited

FOREIGN PATENT DOCUMENTS

| | | |
|---|---|---|
| DE | 927 629 C | 5/1995 |
| WO | WO 00/37040 | 6/2000 |
| WO | WO 01/08652 | 2/2001 |
| WO | WO 01/17374 | 3/2001 |

OTHER PUBLICATIONS

Neff et al., "Autoxidation of Polyunsaturated Triacylglycerols. I. Trilinoleoylglycerol", Lipds 25: 33–39 (1990).

Sjovall et al., "Reversed–phase high–performance liquid chromatographic separation of tert.–butyl hydroperoxide oxidation products of unsaturated triacyglycerols, "Journal of Chromatography 905: 119–132 (2001).

Lissette Steenhorst–Slikkerveer et al., "Analysis of Non-volatile Lipid Oxidation Products in Vegetable Oils by Normal–Phase High–Performance Liquid Chromatography with Mass Spectrometric Detection1," JAOCS 77: 837–845 (2000).

Dong Ki Park et al., "High Performance Liquid Chromatography of Hydroperoxides Formed by Autoxidation of Vegetable Oils," Agric. Biol. Chem. 45: 2443–2448 (1981).

Kenneth Peers et al., "Controlled synthesis of monohydroperoxides by alpha–tocopherol inhibited autoxidation of polyunsaturated lipids," Chemistry and Physics of Lipids 32: 49–56 (1983).

Naomichi Baba et al., "Chemoenzymatic Syntheses of Triacylglyceride Hydroperoxides," Biosci. Biotech. Biochem. 56: 1694–1695 (1992).

Naomachi Baba et al., "Synthesis of Triacylglyceride Hydroperoxides Derived from Linoleic Acid," Biosci. Biotech. Biochem. 58: 1547–1548 (1994).

J. Zhu et al., "An Electron Spin Resonance Study of the Reactions of Lipid Peroxyl Radicals with Antioxidants," J. Phys. Chem. 94: 7185–7190 (1990).

*Primary Examiner*—Deborah D. Carr
(74) *Attorney, Agent, or Firm*—Medlen & Carroll, LLP

(57) ABSTRACT

The present invention relates to the field of human and animal nutrition, and in particular to certain novel compositions of conjugated linoleic acids (CLA). In particular, the present invention relates certain isomers of conjugated linoleic acids at either the SN1 and SN3 or SN2 positions of the acylglyceride molecule and another fatty acyl residue at the other of the SN1 and SN3 or SN2 positions of the acylglyceride molecule. These novel acylglyceride compositions containing conjugated linoleic acyl residues, medium chain fatty acyl residues, long chain fatty acyl residues, and ω3, ω6, and ω9 fatty acyl residues are efficacious as pharmaceutical compositions, animal feed additives, and human dietary supplements.

9 Claims, No Drawings

FUNCTIONAL ACYLGLYCERIDES

This application is a continuation of U.S. application Ser. No. 09/989,835, filed Nov. 20, 2001 now U.S. Pat. No. 6,677,470, allowed.

FIELD OF THE INVENTION

The present invention relates to the field of human and animal nutrition, and in particular to certain novel compositions of conjugated linoleic acids (CLA). In particular, the present invention relates to certain isomers of conjugated linoleic acids at either the SN1 and SN3 or SN2 positions of the acylglyceride molecule and another fatty acyl residue at the other of the SN1 and SN3 or SN2 positions of the acylglyceride molecule.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labeled uptake studies that the 9,11 isomer appears to be somewhat preferentially taken up and incorporated into the phospholipid fraction of animal tissues, and to a lesser extent the 10,12 isomer. (Ha, et al., Cancer Res., 50: 1097 [1990]).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Birt, et al., Cancer Res., 52: 2035s [1992]. Ha, et al., Cancer Res., 50: 1097 [1990] reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr., 66 (6 Supp): 1523s [1997]).

Although the mechanisms of CLA action are still obscure, there is evidence that some component(s) of the immune system may be involved, at least in vivo. U.S. Pat. No. 5,585,400 (Cook, et al., incorporated herein by reference), discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al., incorporated herein by reference, disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066, incorporated herein by reference, describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.), incorporated herein by reference, discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al., incorporated herein by reference), provided data showing that incorporation of CLA into animal feed (birds and mammals) increased the efficiency of feed conversion leading to greater weight gain in the CLA supplemented animals.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., J. Dairy Sci., 43: 231 [1990] observed that processing of milk into yogurt resulted in a concentration of CLA. (Shanta, et al., Food Chem., 47: 257 [1993]) showed that a combined increase in processing temperature and addition of whey increased CLA concentration during preparation of processed cheese. In a separate study, Shanta, et al., J. Food Sci., 60: 695 [1995] reported that while processing and storage conditions did not appreciably reduce CLA concentrations, they did not observe any increases. In fact, several studies have indicated that seasonal or interanimal variation can account for as much as three fold differences in CLA content of cows milk. (See e.g., Parodi, et al., J. Dairy Sci., 60: 1550 [1977]). Also, dietary factors have been implicated in CLA content variation, as noted by Chin, et al., J. Food Camp. Anal., 5: 185 [1992]. Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. However, this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., J. Nutrition, 56: 1191 [1966] isolated a rumen bacterium, *Butyrivibrio fibrisolvens*, which catalyzes formation of 9,11-CLA as an intermediate in the biohydrogenation of linoleic acid. Chin, et al., *J. Nutrition*, 124: 694 [1994] further found that CLA found in the tissues of rodent was associated with bacteria, since corresponding germ-free rats produced no CLA.

While the free fatty acid forms of conjugated linoleic acid described above are suitable for some uses, what is needed in the art are forms of conjugated linoleic acid tailored for particular purposes.

SUMMARY OF THE INVENTION

The present invention relates to the field of human and animal nutrition, and in particular to certain novel compositions of conjugated linoleic acids (CLA). In particular, the present invention relates to certain isomers of conjugated linoleic acids at either the SN1 and SN3 or SN2 positions of the acylglyceride molecule and another fatty acyl residue at the other of the SN1 and SN3 or SN2 positions of the acylglyceride molecule.

Accordingly, in some embodiments, the present invention provides acylglycerides having the following structure:

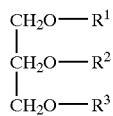

wherein R1 and R3 are acyl residues selected from the group consisting of 10,12; 9,11; 8,10; and 11,13 octadecadienoate and R2 is selected from the group consisting of long chain and medium chain fatty acyl residues. The present invention is not limited to acylglycerides containing any particular medium chain fatty acyl residue. Indeed, a variety of medium chain fatty acyl residues are contemplated including, but not limited to, residues of the following acids: decanoic acid, undecanoic acid, 10-undecanoic acid, lauric acid, cis-5-dodecanoic acid, tridecanoic acid, myristic acid, and myristoleic acid. The present invention is not limited to acylglycerides containing any particular long chain fatty acyl residue. Indeed, a variety of long chain fatty acyl residues are contemplated including, but not limited to, residues of the following acids: pentadecanoic acid, palmitic acid, palmitoleic acid, heptadecanoic acid, stearic acid, elaidic acid, oleic acid, nonadecanoic acid, eicosanoic acid, cis-11-eicosenoic acid, 11,14-eicosadienoic acid, heneicosanoic acid, docosanoic acid, erucic acid, tricosanoic acid, tetracosanoic acid, nervonic acid, pentacosanoic acid, hexacosanoic acid, heptacosanoic acid, octacosanoic acid, nonacosanoic acid, triacosanoic acid, vaccenic acid, tariric acid, and ricinoleic acid. The present invention also contemplates powders, oils, food compositions, and pharmaceutical compositions comprising the foregoing acylglycerides. In some embodiments, these compositions further comprise an antioxidant. In some particularly preferred embodiments, the food composition is a functional food, nutritional supplement food, infant food, pregnancy food, or elderly food. In other preferred embodiments, the nutritional or pharmaceutical compositions comprise one of the forgoing acylglycerides and a carrier suitable for oral, intraintestinal, or parenteral administration.

In still other embodiments, the present invention provides acylglycerides having the following structure:

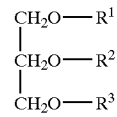

wherein R1 and R3 are acyl residues selected from the group consisting of medium chain and long claim fatty acyl residues and R2 is selected from the group consisting of 10,12; 9,11; 8,10; and 11,13 octadecadienoate residues. The present invention is not limited to acylglycerides containing any particular medium chain fatty acyl residue. Indeed, a variety of medium chain fatty acyl residues are contemplated including, but not limited to, residues of the following acids: decanoic acid, undecanoic acid, 10-undecanoic acid, lauric acid, cis-5-dodecanoic acid, tridecanoic acid, myristic acid, and myristoleic acid. The present invention is not limited to acylglycerides containing any particular long chain fatty acyl residue. Indeed, a variety of long chain fatty acyl residues are contemplated including, but not limited to, residues of the following acids: pentadecanoic acid, palmitic acid, palmitoleic acid, heptadecanoic acid, stearic acid, elaidic acid, oleic acid, nonadecanoic acid, eicosanoic acid, cis-11-eicosenoic acid, 11,14-eicosadienoic acid, heneicosanoic acid, docosanoic acid, erucic acid, tricosanoic acid, tetracosanoic acid, nervonic acid, pentacosanoic acid, hexacosanoic acid, heptacosanoic acid, octacosanoic acid, nonacosanoic acid, triacosanoic acid, vaccenic acid, tariric acid, and ricinoleic acid. The present invention also contemplates powders, oils, food compositions, and pharmaceutical compositions comprising the foregoing acylglycerides. In some embodiments, these compositions further comprise an antioxidant. In some particularly preferred embodiments, the food composition is a functional food, nutritional supplement food, infant food, pregnancy food, or elderly food. In other preferred embodiments, the nutritional or pharmaceutical compositions comprise one of the forgoing acylglycerides and a carrier suitable for oral, intraintestinal, or parenteral administration.

In still other embodiments, the present invention provides acylglycerides having the following structure:

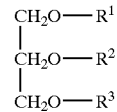

wherein R1 and R3 are acyl residues selected from the group consisting of 10,12; 9,11; 8,10; and 11,13 octadecadienoate and R2 is selected from the group consisting of ω3, ω6, and ω9 fatty acyl residues. The present invention is not limited acylglycerides comprising any particular ω3 fatty acyl residue. Indeed, acylglycerides comprising a variety of ω3 fatty acyl residues are contemplated, including those selected from the group consisting of 9,12,15-octadecatrienoate; 6,9,12,15-octadecatetraenoate; 11,14,17-eicosatrienoate; 8,11,14,17-eicosatetraenoate; 5,8,11,14,17-eicosapentaenoate; 7,10,13,16,19-docosapentaenoate; and 4,7,10,13,16,19-docosahexaenoate. The present invention is not limited to acylglycerides comprising and particular ω6 fatty acyl residue. Indeed, acylglycerides comprising a variety of ω6 fatty acyl residues are contemplated, including those selected from the group consisting of 6,9,12-octadecatrienoate; 8,11,14-eicosatrienoate; 5,8,11,14-eicosatetraenoate; 7,10,13,16-docosatetraenoate and 4,7,10,13,16-docosapentaenoate. The present invention is not limited to acylglycerides comprising and particular ω9 fatty acyl residue. Indeed, acylglycerides comprising a variety of ω9 fatty acyl residues are contemplated, including those selected from the group consisting of 6,9-octadecadienoate; 8,11-eicosadienoate; and 5,8,11-eicosatrienoate. The present invention also contemplates powders, oils, food compositions, and pharmaceutical compositions comprising the foregoing acylglycerides. In some embodiments, these compositions further comprise an antioxidant. In some particularly preferred embodiments, the food composition is a functional food, nutritional supplement food, infant food, pregnancy food, or elderly food. In other preferred embodiments, the nutritional or pharmaceutical compositions comprise one of the forgoing acylglycerides and a carrier suitable for oral, intraintestinal, or parenteral administration.

In still further embodiments, the present invention provides acylglycerides having the following structure:

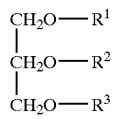

wherein R1 and R3 are acyl residues selected from the group consisting of ω3, ω6, and ω9 fatty acyl residues and R2 is selected from the group consisting 10,12; 9,11; 8,10; and 11,13 octadecadienoate residues. The present invention is not limited acylglycerides comprising any particular ω3 fatty acyl residue. Indeed, acylglycerides comprising a variety of ω3 fatty acyl residues are contemplated, including those selected from the group consisting of 9,12,15-octadecatrienoate; 6,9,12,15-octadecatetraenoate; 11,14,17-eicosatrienoate; 8,11,14,17-eicosatetraenoate; 5,8,11,14,17-eicosapentaenoate; 7,10,13,16,19-docosapentaenoate; and 4,7,10,13,16,19-docosahexaenoate. The present invention is not limited to acylglycerides comprising and particular ω6 fatty acyl residue. Indeed, acylglycerides comprising a variety of ω6 fatty acyl residues are contemplated, including those selected from the group consisting of 6,9,12-octadecatrienoate; 8,11,14-eicosatrienoate; 5,8,11,14-eicosatetraenoate; 7,10,13,16-docosatetraenoate and 4,7,10,13,16-docosapentaenoate. The present invention is not limited to acylglycerides comprising and particular ω9 fatty acyl residue. Indeed, acylglycerides comprising a variety of ω9 fatty acyl residues are contemplated, including those selected from the group consisting of 6,9-octadecadienoate; 8,11-eicosadienoate; and 5,8,11-eicosatrienoate. The present invention also contemplates powders, oils, food compositions, and pharmaceutical compositions comprising the foregoing acylglycerides. In some embodiments, these compositions further comprise an antioxidant. In some particularly preferred embodiments, the food composition is a functional food, nutritional supplement food, infant food, pregnancy food, or elderly food. In other preferred embodiments, the nutritional or pharmaceutical compositions comprise one of the forgoing acylglycerides and a carrier suitable for oral, intraintestinal, or parenteral administration.

In still other embodiments, the present invention provides acylglycerides having the following structure:

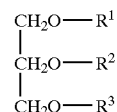

wherein R1 and R3 are 10,12 octadecadienoate and R2 is 9,11 octadecadienoate. In some preferred embodiments, the 10,12 octadecadienoate is t10,c12 octadecadienoate and the 9,11 octadecadienoate is c9,t11 octadecadienoate.

In some embodiments, the present invention provides acylglycerides having the following structure:

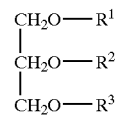

wherein R1 and R3 are 9,11 octadecadienoate and R2 is 10,12 octadecadienoate. In some preferred embodiments, the 10,12 octadecadienoate is t10,c12 octadecadienoate and the 9,11 octadecadienoate is c9,t11 octadecadienoate.

Definitions

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11, 13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "isomerized conjugated linoleic acid" refers to CLA synthesized by chemical methods (e.g., aqueous alkali isomerization, non-aqueous alkali isomerization, or alkali alcoholate isomerization).

As used herein, the term "conjugated linoleic acid moiety" refers to any compound or plurality of compounds containing conjugated linoleic acids or derivatives. Examples include, but are not limited to fatty acids, alkyl esters, and triglycerides of conjugated linoleic acid.

As used herein, it is intended that "triglycerides" or "acylglycerides" of CLA contain CLA at any or all of three positions (e.g., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,c10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, and trans-trans octadecadienoic acids. As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA), triglycerides, or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" refers to a food product to which a biologically active supplement has been added.

As used herein, the term "infant food" refers to a food product formulated for an infant such as formula.

As used herein, the term "elderly food" refers to a food product formulated for persons of advanced age.

As used herein, the term "pregnancy food" refers to a food product formulated for pregnant women.

As used herein, the term "nutritional supplement" refers to a food product formulated as a dietary or nutritional supplement to be used as part of a diet.

As used herein, the term "medium chain fatty acyl residue" refers to fatty acyl residues derived from fatty acids with a carbon chain length of equal to or less than 14 carbons.

As used herein, the term "long chain fatty acyl residue" refers to fatty acyl residues derived from fatty acids with a carbon chain length of greater than 14 carbons.

As used herein, the term "volatile organic compound" refers to any small carbon-containing compound which exists partially or completely in a gaseous state at a given temperature. Volatile organic compounds may be formed from the oxidation of an organic compound (e.g., CLA). Volatile organic compounds include, but are not limited to pentane, hexane, heptane, 2-butenal, ethanol, 3-methyl butanal, 4-methyl pentanone, hexanal, heptanal, 2-pentyl furan, octanal.

As used herein, the term "metal oxidant chelator" refers to any antioxidant that chelates metals. Examples include, but are not limited to lecithin and citric acid esters.

As used herein, the term "alcoholate catalyst" refers to alkali metal compounds of any monohydric alcohol, including, but not limited to, potassium methylate and potassium ethylate.

DETAILED DESCRIPTION OF THE INVENTION

The present invention relates to the field of human and animal nutrition, and in particular to certain novel compositions of conjugated linoleic acids (CLA). In particular, the present invention relates to certain isomers of conjugated linoleic acids at either the SN1 and SN3 or SN2 positions of the acylglyceride molecule and another fatty acyl residue at the other of the SN1 and SN3 or SN2 positions of the acylglyceride molecule.

I. Sources of Conjugated Linoleic Acids

The acylglycerides of the present invention contain conjugated linoleic acyl residues. The conjugated linoleic acid incorporated in these acylglycerides may be made by a variety of methods, for example, those described in U.S. Pat. Nos. 6,015,833 and 6,060,514, each of which is herein incorporated by reference. In some embodiments, sunflower oil, safflower oil, or corn oil are reacted at an ambient pressure under an inert gas atmosphere with an excess of alkali in a high-boiling point solvent, namely propylene glycol at a temperature below the boiling point of the solvent. In some particularly preferred embodiments, sunflower oil, safflower oil, or corn oil are reacted in the presence of an alkali alcoholate catalyst and a small amount of a suitable solvent. As compared to soybean oil, these oils have lower concentrations of undesirable components such as phosphatides and sterols. These undesirable components may contribute to the formation of gums which foul the conjugation equipment and other undesirable polymers.

A. Isomerization with Propylene Glycol as a Solvent

In some embodiments of the present invention, the conjugated linoleic acid is produced by nonaqueous alkali isomerization. The reaction conditions of the controlled isomerization process allow for precise control of the temperature (and constant ambient pressure) of the conjugation process. Preferably the alkali is an inorganic alkali such as potassium hydroxide, cesium hydroxide, cesium carbonate or an organic alkali such as tetraethyl ammonium hydroxide. The catalyst is preferably provided in a molar excess as compared to the fatty acid content of oil. The solvent is propylene glycol. Preferably, the reaction is conducted within a temperature range 130 to 165° C., most preferably at about 150° C. The time of the reaction may vary, however, there is an increased likelihood of the formation of undesirable isomers when the reaction is conducted for long periods of time. A relatively short reaction time of 2.0 to 6.5 hours has proved satisfactory for excellent yields.

It will be understood to a person skilled in the art that to produce the desired composition, the reaction conditions described above may be varied depending upon the oil to be conjugated, the source of alkali, and equipment. Preanalysis of a particular oil may indicate that the conditions must be varied to obtain the desired composition. Therefore, the temperature range, pressure, and other reaction parameters represent a starting point for design of the individual process and are intended as a guide only. For example, it is not implied that the described temperature range is the only range which may be used. The essential aspect is to provide precise temperature control. However, care must be taken because increasing the pressure may lead to less than complete isomerization and the formation of undesirable isomers. Finally, the length of the conjugation reaction may be varied. Generally, increasing amounts of undesirable isomers are formed with increasing length or reaction time. Therefore, the optimal reaction time allows the reaction to go nearly or essentially to completion but does not result in the formation of undesirable isomers.

Following the conjugation reaction, the resulting CLA containing composition may be further purified. To separate the fatty acids from the conjugation reaction mix, the reaction mix is cooled to approximately 95° C., an excess of water at 50° C. is added, and the mixture slowly stirred while the temperature is reduced to about 50° C. to 60° C. Upon addition of the water, a soap of the fatty acids is formed and glycerol is formed as a by-product. Next, a molar excess of concentrated HCl is added while stirring. The aqueous and nonaqueous layers are then allowed to separate at about 80–90° C. The bottom layer containing water and propylene glycol is then drawn off. The remaining propylene glycol is removed by vacuum dehydration at 60–80° C.

The dried CLA composition may then preferably be degassed in degassing unit with a cold trap to remove any residual propylene glycol. Next, the CLA is distilled at 190° C. in a molecular distillation plant at a vacuum of $10^{-1}$ to $10^{-2}$ millibar. The advantage of this purification system is the short time (less than one minute) at which the CLA is held at an elevated temperature. Conventional batch distillation procedures are to be strictly avoided since they involve an elevated temperature of approximately 180–200° C. for up to several hours. At these elevated temperatures the formation of undesirable trans-trans isomers will occur. Approximately 90% of the feed material is recovered as a slightly yellow distillate. The CLA may then be deodorized by heating to about 120°–170° C., preferably at about 150° C. for 2 hours to improve smell and taste. Excessive heat may result in the formation of trans-trans isomers. These procedures produce a CLA composition with a solvent level of less than about 5 ppm, preferably less than about 1 ppm. This process eliminates toxic trace levels of solvent so that the resulting composition is essentially free of toxic solvent residues.

The processes described above are readily adaptable to both pilot and commercial scales. For example, 400 kg of safflower oil may be conjugated at 150° C. for 5 hours in 400 kg of propylene glycol with 200 kg KOH added as a catalyst. The resulting CLA may then be purified as described above. Further, commercial scale batch systems may be easily modified to produce the desired CLA composition. For example, stainless steel reactors should be preferably glass lined to prevent corrosion due to pH levels of below 3.0. However, it should be noted that conjugation processes utilizing nonaqueous solvents are generally less corrosive than those conducted with water.

B. Isomerization with Alcoholate Catalysts

In other embodiments, the acylglycerides of the present invention incorporate acylglycerides made by the isomerization of linoleic acid in the presence alcoholate catalysts. After fat splitting and dehydration, the free fatty acids are combined with methanol or another monohydric low molecular weight alcohol and heated to the temperature at which the alcohol boils. Esterification proceeds under refluxing conditions with removal of the reaction water through a condenser. After the addition of a further quantity of the same or a different monohydric alcohol an alcoholate catalyst is blended into the ester mix (See, e.g., U.S. Pat. No. 3,162,658, incorporated herein by reference). Typical alcoholate catalysts are sodium or potassium ethoxide, or their methyl, butyl, or propyl counterparts.

In the esterification, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, product of varying viscosity can be used to obtain the desired flow or compounding characteristics without affecting the therapeutic or nutritional properties arising from the CLA moieties. The theory and practice of esterification are conventional. A basic explanation of the most common methods is set forth in the McCraw-Hill Encyclopedia of Science & Technology, McGraw-Hill Book Co., N.Y.: 1996 (5th ed.). The animal and human body has a variety of esterases, so that the CLA-ester is cleaved to release the free fatty acids readily. Tissue uptake may have a different kinetics depending on the tissue involved and the benefit sought.

In the isomerization step, it was found that alcoholate catalysis produced a much superior product than aqueous alkali mediated isomerization. The latter process always produced undesirable isomers even under mild reaction conditions. The milder conditions do give lower amounts of unwanted isomers, but at the great expense of yield, as shown in the Examples. In most systems the appearance of the c9,t11 and t10,c12 isomers dominates and they are formed in roughly equimolar amounts. It has not heretofore been possible to control the isomerization of the one isomer to the exclusion of the other. While it is desirable to increase the percentage of one or the other isomer (depending on the physiological effect to be achieved), at present this must largely be carried out by adding an enriched source of the desired isomer.

The preferred starting materials for conjugation with alcoholate catalysts are sunflower oil, safflower oil, and corn oil. Each of these oils contains high levels of linoleic acid and low levels of linolenic acid. Conjugation of linolenic acid results in the formation of several uncharacterized fatty acid moieties, the biological properties of which are unknown. Previous conjugation processes were not concerned with the production of unknown compounds because the products were used in drying oils, paints and varnishes and not in products destined from human or animal consumption.

In some embodiments, it is further contemplated that glycerol and esters of glycerol should be removed before making monoesters of fatty acids. Traces of glycerol present during conjugation contribute to the production of trimethoxypropane and triethoxypropane. Therefore, prior to conjugation, it is preferable to distill monoesters obtained by alcoholysis.

C. Synthesis of Other CLA Isomers

The present invention also contemplates the synthesis of triglycerides comprising the isomers listed in Table 1 below. In some embodiments of the invention, a partially purified or concentrated isomer of CLA is treated under conditions that cause migration of the double bond system. In preferred embodiments, the conditions comprise heating at least one isomer to about 200–240° C., preferably to about 220° C. In other embodiments, the conditions further comprise reacting the partially purified or concentrated isomer or isomers under nitrogen in a sealed container. Referring to Table 1, the preparations of isomers in column 1 can be used to produce preparations containing a substantial amount of the corresponding isomer in column 2. After the initial conversion reaction, the preparation will contain both the starting isomer and the "sister" isomer. Likewise, the preparations of isomers in column 2 can be used to produce substantial amounts of the corresponding isomer in column 1. The preparations containing both isomers may be further treated to purify the sister isomer (e.g., by gas chromatography). As will be understood by those skilled in the art, it is possible to start with more than one partially purified isomer, thereby producing a preparation containing four, six, eight or more isomers. In further embodiments, a purified preparation of the sister isomer may be prepared by methods known in the art (i.e., gas-liquid chromatography) from the treated preparation containing the initial isomer and its sister isomer.

TABLE 1

| Column 1 | Column 2 |
|---|---|
| c9, t11 | t8, c10 |
| t10, c12 | c11, t13 |
| c7, t9 | t6, c8 |
| t11, c13 | c12, t14 |
| c6, t8 | t5, c6 |
| c5, t7 | t4, c6 |
| c4, t6 | t3, c5 |
| t12, c14 | c13, t15 |
| t13, c15 | c14, t16 |

As demonstrated in the Examples, treatment of purified t10,c12 octadecadienoic acid resulted in the production of c11,t13 octadecadienoic acid. Likewise, concentrated or partially purified c11,t13 octadecadienoic acid can be used to produce t10,c12 octadecadienoic acid.

D. Other Sources of Conjugated Linoleic Acid Isomers

In other embodiments, the conjugated linoleic acids used to produce the acylglycerides of the present invention are obtained from alternative sources. For example, some isomers (e.g., t10,c12 and c9,t11) are available from commercial sources. In other embodiments, t10,c12 and c9,t11 CLA may be purified by the methods described in Scholfield et al., JAOCS 47(8):303 (1970) and Berdeau et al., JAOCS 74:1749–55 (1998). This method allows for the crystallization and precipitation of the t10,c12 isomer from a mixture of isomers. If the initial mixture contains predominantly the t10,c12 and c9,t11 isomers (i.e., the isomerization id conducted as described above), then the oil remaining after precipitation will be enriched for c9,t11 CLA. In still further embodiments, the CLA isomers may be prepared by gas chromatography or gas chromatography/mass spectrometry procedures.

II. Synthesis of Triglycerides

The present invention provides novel acylglycerides, as well as food compositions, animal feeds, pharmaceutical compositions and nutritional compositions comprising the novel acylglycerides. According to the present invention acylglycerides are provided having the following general structure:

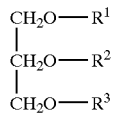

wherein R1 and R3 are acyl residues selected from the group consisting of 10,12; 9,11; 8,10; and 11,13 octadecadienoate and R2 is selected from the group consisting of long chain and medium chain fatty acyl residues.

In other embodiments, acylglycerides having the following general structure are provided:

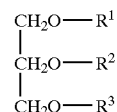

wherein R1 and R3 are acyl residues selected from the group consisting of medium chain and long claim fatty acyl residues and R2 is selected from the group consisting of 10,12; 9,11; 8,10; and 11,13 octadecadienoate residues.

In other embodiments, acylglycerides having the following general structure are provided:

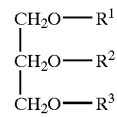

wherein R1 and R3 are acyl residues selected from the group consisting of 10,12; 9,11; 8,10; and 11,13 octadecadienoate and R2 is selected from the group consisting of ω3, ω6, and ω9 fatty acyl residues.

In other embodiments, acylglycerides having the following general structure are provided:

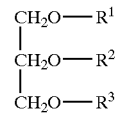

wherein R1 and R3 are acyl residues selected from the group consisting of ω3, ω6, and ω9 fatty acyl residues and R2 is selected from the group consisting 10,12; 9,11; 8,10; and 11,13 octadecadienoate residues.

In other embodiments, acylglycerides having the following general structure are provided:

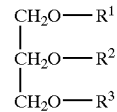

wherein R1 and R3 are 10,12 octadecadienoate and R2 is 9,11 octadecadienoate.

In other embodiments, acylglycerides having the following general structure are provided:

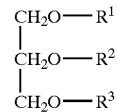

wherein R1 and R3 are 9,11 octadecadienoate and R2 is 10,12 octadecadienoate.

The present invention is not limited to acylglycerides comprising residues of any particular isomer of conjugated linoleic acid. Indeed, the use of a variety of isomers of conjugated linoleic acid is contemplated, including, but not limited to t10,c12 octadecadienoate; c10,t12 octadecadienoate; c9,t11 octadecadienoate; t9,c11 octadecadienoate; c8,t10 octadecadienoate; t8,c10 octadecadienoate; t11,c13 octadecadienoate; and c11,t13 octadecadienoate, as well as the other isomers listed in Table 1 above.

The present invention is not limited to acylglycerides comprising any particular long chain or medium chain fatty acid residues. Indeed, the incorporation of a variety long chain and medium chain fatty acid residues is contemplated, including, but not limited to decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecanoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), vaccenic acid (t-11-octadenecoic acid, 18:1), tariric acid (octadec-6-ynoic acid, 18:1), and ricinoleic acid (12-hydroxyoctadec-cis-9-enoic acid, 18:1).

The present invention is not limited to acylglycerides comprising any particular ω3, ω6, and ω9 fatty acyl residues. Indeed, the present invention encompasses, but is not limited to, acylglycerides including residues of the following ω3, ω6, and ω9 fatty acids:

9,12,15-octadecatrienoic acid (α-linolenic acid) [18:3, ω3];
6,9,12,15-octadecatetraenoic acid (stearidonic acid) [18:4, ω3];
11,14,17-eicosatrienoic acid (dihomo-α-linolenic acid) [20:3, ω3];
8,11,14,17-eicosatetraenoic acid [20:4, ω3],
5,8,11,14,17-eicosapentaenoic acid [20:5, ω3];
7,10,13,16,19-docosapentaenoic acid [22:5, ω3];
4,7,10,13,16,19-docosahexaenoic acid [22:6, ω3];
9,12-octadecadienoic acid (linoleic acid) [18:2, ω6];
6,9,12-octadecatrienoic acid (γ-linolenic acid) [18:3, ω6];
8,11,14-eicosatrienoic acid (dihomo-γ-linolenic acid) [20:3 ω6];
5,8,11,14-eicosatetraenoic acid (arachidonic acid) [20:4, ω6];
7,10,13,16-docosatetraenoic acid [22:4, ω6];
4,7,10,13,16-docosapentaenoic acid [22:5, ω6];
6,9-octadecadienoic acid [18:2, ω9];
8,11-eicosadienoic acid [20:2, ω9]; and
5,8,11-eicosatrienoic acid (Mead acid) [20:3, ω9].

Moreover, acyl residues may be hydroxylated, epoxidated or hydroxyepoxidated acyl residues.

In some embodiments of the present invention, the novel acylglycerides of the present invention are prepared by chemical method synthesis. These methods and interemediates for use therein are described in examples 8–20.

In other embodiments, novel acylglycerides of the present invention are manufactured by using non-specific and position-specific lipases to insert a first fatty acyl residue at position 2 (SN2) of the acylglyceride and a second fatty acyl residue at positions 1 and 3 (SN1 and SN3) of the acylgyceride. Non-specific lipases are lipases that are able to hydrolyse or esterify (i.e., the reverse reaction) fatty acids in all positions on a glycerol. A position-specific or 1,3 specific lipase almost exclusively hydrolyses or esterifies fatty acids in position 1 and 3 on the glycerol backbone. The structured acylglycerides of the present invention are synthesized by first using a non-specifc lipase to attach the desired fatty acid for position 2 to all 3 positions and then hydrolysing the acyl residues in position 1 and 3 using a 1,3 specific lipase. The hydrolysed acids are then removed by distillation before the acids desired to be attached to positions 1 are 3 are added and esterified to position 1 and 3 by the same lipase. The direction of the reaction (hydrolysis or esterification) is easily controlled by water addition or removal respectively. In the following example is a general outline of the method.

In particularly preferred embodiments, a purified aliquot of a first fatty acid (about 3 moles), glycerol (about 1 mole) and up to 10% by weight of acids are mixed with immobilized non-specific lipase (commercially available). The mixture is stirred under vacuum and slightly heated (50–60° C.). The water produced during the esterification is continuously removed by the vacuum suction. After 24–48 hours, the reaction is finished and the enzymes are removed and recovered by filtration. The resulting acylglyceride has the first fatty acid attached at all three positions. The first fatty acid residue at positions 1 and 3 is then removed in by addition of 1,3 specific immobilized lipase (commercially available) and 1% water. The mixture is heated to 50–60° C. and stirred under nitrogen atmosphere for 24–48 hours. The reaction mixture now comprises free fatty acids liberated from position 1 and 3 and monoglycerides (fatty acid B attached to position 2). Next, in preferred embodiments, the fatty acids are distilled off from the mixture by molecular distillation. In further preferred embodiments, about one mole of the monoglyceride is allowed to react for 24–48 hours with 2 moles a second free fatty acid in the presence of 1,3 specific lipase. In some embodiments, this reaction takes place under stirring and vacuum at 50–60° C. to remove water produced in the esterification process. The resulting acylglyceride is a structured triglyceride with the first fatty acid in position 2 and the second fatty acid in positions 1 and 3.

As described above, in some embodiments of the present invention, lipase that specifically acts on the positions 1 and 3 of triglyceride is used as catalyst. The present invention is not limited to the use of any particular 1,3 specific lipase. Examples of 1,3 specific lipases useful in the present invention include lipases produced by a microorganism belonging to the genus Rhizopus, Rhizomucor, Mucor, Penicillium, Aspergillus, Humicola or Fusarium, as well as porcine pancreatic lipase. Examples of commercially available lipases include lipase of *Rhizopus delemar* (Tanabe Pharmaceutical, Dalipase), lipase of *Rhizomucor miehei* (Novo Nordisk, Ribozyme IM), lipase of *Aspergillus niger* (Amano Pharmaceutical, Lipase A), lipase of *Humicola lanuginosa* (Novo Nordisk, Lipolase), lipase of *Mucor javanicus* (Amano Pharmaceutical, Lipase M) and lipase of *Fusarium heterosporum*. These lipases may be used in their native form, or in the form of lipase that has been immobilized on cellite, ion exchange resin or a ceramic carrier.

The amount of water added to the reaction system affects the outcome of the reaction. Transesterification does not proceed in the absolute absence of water, while if the amount of water is too much, hydrolysis occurs, the triglyceride recovery rate decreases, or spontaneous acyl group transfer occurs in a partially acylated glyceride resulting in transfer of the saturated fatty acid at the position 2 to the position 1 or 3. Thus, when using an immobilized enzyme that does not have bonded water, it is effective to first activate the enzyme using a substrate to which water has been added before carrying out the reaction, and then use a substrate to which water is not added during the reaction. In order to activate the enzyme in batch reactions, a substrate containing water at 0 to 1,000% (wt %) of the amount of added enzyme should be used to pretreat the enzyme, and in the case of activating by a column method, a water-saturated substrate should be allowed to continuously flow through the column. The amount of lipase used in a batch reaction may be determined according to the reaction conditions. Although there are no particular limitations on the amount of lipase, 1 to 30% (wt %) of the reaction mixture is suitable when using, for example, lipase of *Rhizopus delemar* or lipase of *Rhizomucor miehei* immobilized on cellite or a ceramic carrier.

In some preferred embodiments, the above-mentioned immobilized enzyme can be used repeatedly. Namely, the reaction can be continued by leaving the immobilized enzyme in a reaction vessel after reaction and replacing the reaction mixture with freshly prepared reaction mixture comprising substrate. In addition, for transesterification by a column method, a reaction mixture containing substrate be allowed to flow continuously at the rate of 0.05 to 20 ml/hr per gram of enzyme. In other preferred embodiments, the content of target triglyceride can be increased by performing transesterification repeatedly. Namely, lipase specifically acting on the positions 1 and 3 of the acylglyceride is allowed to act in the presence of the second fatty acid or an ester thereof to obtain a reaction mixture in which fatty acids at positions 1 and 3 are transesterified to the desired fatty acid.

The target acylglycerides of the present invention can easily be isolated by routine methods such as liquid chromatography, molecular distillation, downstream membrane fractionation or vacuum superfractionation or a combination thereof. Purification of the target acylglycerides of the present invention can be performed by alkaline deacidation, steam distillation, molecular distillation, downstream membrane fractionation, vacuum superfractionation, column chromatography, solvent extraction or membrane separation, or a combination thereof so as to remove the above-mentioned fatty acids released by the transesterification and unreacted unsaturated fatty acids.

III. Stabilization of CLA Acylglycerides

The present invention also contemplates stabilization of the CLA acylglycerides by preventing oxidation of the compounds. The present invention is not limited to any one mechanism. Indeed, an understanding of the mechanism of the invention is not necessary to produce the composition or perform the methods of the present invention. Nevertheless, unlike non-conjugated fatty acids, CLA does not appear to form peroxide breakdown products. This was demonstrated experimentally by measuring peroxide values (PV) spectrophotometrically by a chlorimetirc ferric thiocyanate method. After storage in open glass, the PV of CLA was 32; in comparison, the value for linoleic acid was 370.

CLA forms volatile organic compounds during breakdown, including hexane. Products stored in a steel drum for several weeks were found to contain up to 25 ppm hexane. Hexane has a characteristic taste and smell that is undesirable in food products. Oxidation of CLA appears to be caused by the presence of metal contaminants. Thus, a system for removal of such compounds that promote oxidation during purification is advantageous.

Furthermore, it is also advantageous to add compounds to CLA acylglycerides to decrease oxidation during storage. Compounds that prevent oxidation (antioxidants) have two general mechanisms of action. The first is the prevention of oxidation by lipid peroxide radical scavenging. Examples include but are not limited to tocopherols and ascorbylpalmitate. The second mechanism for preventing oxidation is by the chelation of metal ions. Examples of metal oxidant chelators include, but are not limited to, citric acid esters and lecithin. Some commercially available compounds (e.g., Controx, Grumau (Henkel), Illertissen, Del.) include both peroxide scavengers and metal chelators (e.g., lecithin, tocopherols, ascorbylpalmitate, and citric acid esters). In some embodiment of the present invention, metal oxidant chelators are added to CLA containing compounds to prevent oxidation. In other embodiments, a combination of metal oxidant chelators and peroxide scavengers is included in the CLA acylglyceride composition.

In some embodiments, gas chromatography/mass spectroscopy is used in detect the presence of volatile organic breakdown products of CLA. In other embodiments, oil stability index (OSI) measurements are used to detect the presence of volatile organic breakdown products of CLA. In some embodiments of the present invention, pro-oxidants (e.g., iron) are removed from the CLA acylglyceride compositions. Methods for removing pro-oxidants include, but are not limited to, distillation or by adsorption. In some embodiments of the present invention, compounds are added to prevent oxidation of CLA.

In preferred embodiments, precautions are taken during purification to prevent oxidation during storage. These precautions include the removal of compounds that serve as pro-oxidants, including but not limited to iron or other metals. In some embodiments, metals are removed by treating with adsorbing agents, including but not limited to bleaching earth, active charcoal zeolites, and silica. In other embodiments, the pro-oxidants are removed by distillation.

In some embodiments, pro-oxidants are removed in a distillation process. In some preferred embodiments, distillation of a CLA acylglyceride of the present invention is performed on a molecular distillation apparatus. Distillation is carried out at 150° C. and a pressure of $10^{-2}$ mbar. The present invention is not intended to be limited to the conditions described for distillation. Other temperatures and pressures are within the scope of the present invention.

In some embodiments, oxidation of the CLA acylglycerides of the present invention is prevented by the addition of metal oxidant chelators or peroxide scavengers to the finished product. In some embodiments, the amount of oxidation is measured by the oil stability index (OSI). The OSI (See e.g., AOCS official method Cd 12b-92) is a measurement of an oil's resistance to oxidation. It is defined mathematically as the time of maximum change of the rate of oxidation. This rate can be determined mathematically. Experimentally, the OSI is calculated by measuring the change in conductivity of deionized water is which volatile organic acids (oxidation products) are dissolved. When performing OSI measurements, it is important to avoid contamination by trace amounts of metals, which can accelerate the oxidation process. This is generally accomplished by careful washing of all glassware used with a cleaning solution lacking chromate or surfactants. Water must be deionized and all solvents must be of a highly purified grade.

IV. Formulation and Administration of CLA Acylglycerides

The CLA acylglycerides of the present invention may be provided in a variety of forms. In some embodiments, administration is oral. The CLA moieties may be formulated with suitable carriers such as starch, sucrose or lactose in tablets, pills, dragees, capsules, solutions, liquids, slurries, suspensions and emulsions. Preferably, the CLA formulations contain antioxidants, including, but not limited to Controx, Covi-OX, lecithin, and oil soluble forms of vitamin C (ascorbyl palmitate). The CLA acylglyceride may be provided in oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the CLA is provided as soft gelatin capsules containing 500–1500 mg of acylglyceride. The CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

In particularly preferred embodiments, the acylglycerides of the present invention are combined with an excipient or powdering agent. The mixture is then formed into a powder by methods such as spray drying (See, e.g., U.S. Pat. No. 4,232,052, incorporated herein by reference). In general, spray drying involves liquefying or emulsifying a substance and then atomizing it so that all but a small percentage of water is removed, yielding a free flowing powder. Suitable spray drying units include both high pressure nozzle spray driers and spinning disk or centrifugal spray driers. The present inventors have discovered that powders containing high loads (e.g., 40%–65%) conjugated linoleic acid and/or other oils (e.g., evening primrose oil, borage oil, flax oil, CLA oil) can be formed by the simple spray drying of the emulsion of the oil, excipient and water. It is not necessary to incorporate more complex methods involving spraying into a fluidized bed or spraying in a countercurrent fashion.

The present invention is not limited to any particular excipient. Indeed, a variety of excipients are contemplated, including, but not limited to, HI-CAP 100 (National Starch, Bridgewater, N.J.) and HI-CAP 200 (National Starch, Bridgewater, N.J.). The powder of the present invention contains a high percentage of oil as compared to the excipient. In some embodiments, the oil is 20% of the powder on a weight/weight basis (i.e., the powder contains 20 grams of oil for every 100 grams of powder). In other embodiments, the oil is 35% of the powder on weight/weight basis. In still other embodiments, the oil is at least 50% of the powder on a weight/weight basis. In further embodiments, the oil is at least 60%–65% of the powder on a weight/weight basis. In each case, the oil powder is free flowing and odorless. In preferred embodiments, the oil comprises a CLA moiety. In particularly preferred embodiments, the oil comprises CLA acylglyceries of the present invention.

An effective amount of CLA moiety may also be provided as a supplement in various food products, including animal feeds, human functional food products, infant food products, nutritional supplements, and drinks. For the purposes of this application, food products containing CLA acylglycerides means any natural, processed, diet or non-diet food product to which exogenous CLA acylglyceride has been added. Therefore, CLA acylglycerides may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

Furthermore, as shown above and in the Examples, CLA acylglyceride compositions can contain levels of volatile organic compounds that cause the taste and smell of food products containing the CLA acylglyceride to be adversely effected. It is contemplated that the food products of the present invention that contain CLA acylglyceride compositions having less than 100 ppm volatile organic compounds, and preferably less than 5 ppm volatile organic compounds, are superior in taste and smell to food products containing higher levels of volatile organic compounds and will be preferred in blind taste and smell tests. Accordingly, some embodiments of the present invention provide a food product containing a CLA acylglyceride, wherein the conjugated linoleic acid moiety has a sufficiently low volatile organic acid compound concentration so that taste and smell of the food product is not affected.

Experimental

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); µM (micromolar); kg (kilograms); g (grams); mg (milligrams); µg (micrograms); ng (nanograms); L or l (liters); ml (milliliters); µl (microliters); cm (centimeters); mm (millimeters); nm (nanometers); ° C. (degrees centigrade); KOH (potassium hydroxide); HCL (hydrochloric acid); Hg (mercury).

EXAMPLE 1

Isomerization of Safflower Oil Using Propylene Glycol at Low Temperature

Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 µl of purified water in a new test tube and again shaken under nitrogen. The resulting upper layer was then washed of isooctane and decanted into a third test tube. A small amount of sodium sulfate was added for water absorption. A 1 µl sample was then injected directly into the Gas chromatograph.

The gas chromatography conditions were as follows:

| | |
|---|---|
| System: | Perkins-Elmer Auto System |
| Injector: | Splitless at 240° C. |
| Detector: | Flame Ionization Detector at 280° C. |
| Carrier: | Helium |
| Column: | WCOT Fused Silica 0.25 mm X100M, CP-SL 88 for FAME, DF 0.2 |
| Oven Program: | 80° C. (0 min.) increasing to 220° C. at 10° C. per min. and held at 220° C. for 10 min. |

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, *Lipids*, 32 (10) 1019–34 (1997), incorporated herein by reference.

This data, presented in Table 2 and summarized in Table 10, demonstrates that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions.

TABLE 2

| Peak # | Time (Min) | Component Name | Area (%) | Area (µV · s) | Height (µV) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9, c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9, t11 | 36.51 | 1950669.98 | 124313.83 |
| 15 | 78.370 | CLA t10, c12 | 37.16 | 1985488.96 | 132265.33 |
| 16 | 78.664 | CLA c9, c11 | 1.06 | 56583.10 | 5699.43 |
| 17 | 78.880 | CLA c10, c12 | 1.26 | 67503.55 | 4572.65 |
| 18 | 80.102 | CLA t9, t11/ t10, t12 | 0.73 | 39110.00 | 4743.28 |
| 19 | 85.165 | | 0.03 | 1621.65 | 231.32 |
| | | | 100.00 | 5343381.15 | 384147.01 |

EXAMPLE 2

Production of CLA with Alcoholate Catalysts

This example describes the production of CLA from safflower oil using potassium methylate as a catalyst. Distilled methyl ester of sunflower oil (41.5 g) was placed in a reactor with 0.207 g methanol and 0.62 g potassium methylate, and the reactor purged with nitrogen before closing. The contents of the reactor were stirred while to 120° C. The reaction was then allowed to proceed at 120° C. for 4 hours. the reactor was then cooled to 80° C. and the contents were transferred to a separating funnel and washed with hot distilled water and then with hot water containing citric acid. The methylester was then dried under vacuum with moderate heat. The dried methyl ester was dissolved in isooctane and analyzed by GLC with a Perkin Elmer autosampler. The column was a highly polar fused silica type. the following program was used:

| | |
|---|---|
| Injection: | Splitless at 250° C. |
| Detection: | Flame ionization detector at 280° C. |
| Carrier: | Helium at psig. |
| Oven program: | 80° C.–130° C. (45° C./min.), then 1° C./min. to 220° C. and 220° C. throughout for 10 min. |
| Column: | WCOT FUSED SILICA 0.25 mm 100 m, CP-SIL 88 for FAME, df + 0.2. |

The CLA obtained consisted almost exclusively of the c9,t11 and t10,c12 isomers of CLA as shown in Table 3.

TABLE 3

CLA Produced by Isomerization with Potassium-Methylate

| Fatty Acid | Before Isomerization | After Isomerization |
|---|---|---|
| C 16:0 | 5.41 | 5.54 |
| C 18:0 | 3.87 | 3.72 |
| C 18:1 | 29.01 | 29.19 |
| C 18:2, c9, c12 | 59.43 | 0.84 |
| CLA, c9, c11 | 0 | 28.84 |
| CLA, t10, c12 | 0 | 28.45 |
| CLA, c9, c11 | 0 | 0.56 |
| CLA, c10, c12 | 0 | 0.40 |
| CLA, t9, t11; t10, t12 | 0 | 0.27 |

EXAMPLE 3

Production of CLA Powder

This example describes the production of a powder containing CLA acylglycerides of the present invention. The CLA acylglycerides may be prepared as described above. Warm water (538.2 ml at 110–120° F.) and HI-CAP 100 (approximately 230.9 g, National Starch, Bridgewater, N.J.) are combined and agitated until the dispersion is free of any lumps. CLA triglyceride (230.9 g) is then added and the mixture homogenized for 2 min in an Arde Berinco lab homogenizer at setting 30. The pre-emulsion is then homogenized at full speed for 2–5 min (one pass at 3500 psi total pressure). The particle size is checked and should be from about 0.8 to 1.0 microns. The emulsion is then spray dried in a seven foot conical dryer at the following settings: inlet temperature (190–215° C.); outlet temperature (95–100° C.). Outlet temperature is maintained by adjusting the emulsion feed rate. This process produces a free flowing powder containing approximately 50% CLA triglyceride.

EXAMPLE 4

Preparation of CLA Isomers

This Example describes the production c11,t13 octadecadienoic acid from t10,c12 octadecadienoic acid. Fifty grams of KOH were dissolved in propylene glycol under moderate heating. One hundred grams of 98% linoleic acid were then added to the mixture, and the mixture heated to 150° C. and stirred for 3 hours. The mixture was then cooled and washed several times with hot water and then dried under vacuum at moderate heat. The resulting CLA mixture consisted of c9,t11 and t10,c12 octadecadienoic acid as well as traces of CLA isomers. The mixture was converted to methylester by reflux boiling in acidic methanol. Fifty grams of conjugated free fatty acids were dissolved in methanol containing 4.5% sulfuric acid and boiled under reflux conditions for 1 hour in a water bath. The mixture was cooled and the bottom layer discarded. Fresh methanol with 4.5% sulfuric acid was added and the mixture boiled for an additional hour under reflux conditions. After cooling, this methylester mixture was washed several times with water and then dried under vacuum at moderate heat. Ten grams of the methylester were dissolved in acetone and cooled overnight to −60° C. in a freezer. A solid precipitate was recovered by filtration and re-dissolved in acetone and again cooled to −60° C. overnight. The precipitate was dried under vacuum and shown by GLC analysis to contain 97% t10,c12 CLA. The analytical equipment consisted of a Perkin Elmer GLC with autosampler. The column was a highly polar fused silica type. The following program setting were used:

| | |
|---|---|
| Injection: | Splitless at 250° C. |
| Detection: | Flame Ionization Detector at 280° C. |
| Carrier: | Helium at psig. |
| Oven program: | 80° C.–130° C. (45° C./min), then 1° C./min to 220° C. and 220° C. throughout for 10 min. |
| Column: | WCOT FUSED SILICA 0.25 mm × 100 m, CP-SIL 88 for FAME, df = 0.2. |

One gram of purified t10,c12 isomer was then covered with nitrogen in a sealed tube and heated for two hours at 220° C. After cooling, the resulting methylesters were analyzed by GC as above. The relative content of t10,c12 in the mixture was reduced to 52.32% and the c11,t13 isomer was present at a level of 41.96% (See Table 4).

TABLE 4

Conversion of t10, c12 isomer to c11, t13 isomer

| Isomer | % Before heating | % After heating |
|---|---|---|
| c11, t13 | 0 | 41.57 |
| t10, c12 | 97.34 | 51.72 |
| C11, c13 | 0 | 1.44 |
| c10, c12 | 0 | 2.70 |
| t11, t13 | 0 | 0.54 |
| t10, t12 | 0.7 | 1.05 |

EXAMPLE 5

Preparation of CLA Isomers

This Example describes the production t8,c10 octadecadienoic acid from c9,t11 octadecadienoic acid. Purified c9,t11 octadecadienoic acid may be obtained from commercial sources (Matreya, State College, Pa.) or by fermentation with rumen microorganisms (See, e.g., U.S. Pat. No. 5,674,901, incorporated herein by reference). The purified c9,t11 octadecadienoic is converted to a high percentage (e.g., 25% to 50%) t8,c10 octadecadienoic acid by placing the c9,t11 octadecadienoic acid in a sealed tube under nitrogen and heating to 220° C. for about 2 hours.

EXAMPLE 6

Preparation of CLA Isomers

This Example describes the production t6,c8 octadecadienoic acid from c7,t9 octadecadienoic acid. Purified c7,t9 octadecadienoic acid may be obtained by preparative scale gas chromatography. The purified c7,t9 octadecadienoic is converted to a high percentage (e.g., 25% to 50%) t6,c8 octadecadienoic acid by placing the c9,t11 octadecadienoic acid in a sealed tube under nitrogen and heating to 220° C. for about 2 hours.

EXAMPLE 7

Preparation of CLA Isomers

This Example describes the production c12,t14 octadecadienoic acid from t11,c13 octadecadienoic acid. Purified t11,c13 octadecadienoic acid may be obtained by preparative scale gas chromatography (e.g., following the process described in Example 1). The purified t11,c13 octadecadienoic is converted to a high percentage (e.g., 25% to 50%) c12,t14 octadecadienoic acid by placing the c9,t11 octadecadienoic acid in a sealed tube under nitrogen and heating to 220° C. for about 2 hours.

EXAMPLE 8

Intermediates for Chemical Synthesis of Acylglycerols

The following intermediate compounds are useful for the chemical synthesis of triglycerides containing CLA isomers and/or other fatty acids. The use of these intermediates is further described in Examples 12–23.

1,3-dipalmitoyl acetone (Intermediate 1)

1,3-dipalmitoyl acetone is prepared from 1,3-dihydroxy acetone (as a dimer) and palmitoyl chloride with pyridine as base according to P. H. Bentley et al. in J. Org. Chem. 35:2082 (1970).

1,3-di(c9,t11-octadecadienoyl) acetone (Intermediate 2)

The title compound is prepared from 1,3-dihydroxyacetone and c9,t11-octadecadienoyl acid chloride (prepared from the corresponding acid thionyl chloride or phosphorous penta chloride according to standard methods).

1,3-di(t10,c12-octadecadienoyl) acetone (Intermediate 3)

The title compound is prepared as intermediate 2 from t10,c12-octadecadienoid acid and 1,3-dihydroxyacetone.

1,3-palmitoyl glycerol (Intermediate 4)

The title compound is prepared by reduction of 1,3-palmitoyl acetone (Intermediate 1) using sodium borhydride according to P. H. Bentley et al. in J. Org. Chem. 35:2082 (1970).

1,3-di(c9,t11-octadecadienoyl)-glycerol (Intermediate 5)

The title compound is prepared from 1,3-di(c9,t11-octadecadienoyl) acetone (Intermediate 2) according to the method described for Intermediate 4.

1,3-di (t10,c12-octadecadienoyl) glycerol (Intermediate 6)

The title compound is prepared from 1,3-di(t10,c12-octadecadienoyl) acetone (Intermediate 3) according to the method described for Intermediate 4.

1,3-Benzylidene glycerol (Intermediate 7)

1,3-Benzylidene glycerol is prepared from benzaldehyde and anhydros glycerol as described by Hilbert et al in J. Am. Chem. Soc. 51:1601 (1929).

2-Nosyl-1,3-benzylidene glycerol (Intermediate 8)

4-Nitrobenzenesulphonyl chloride (14.7 g, 12 ekv) and benzylidene glycerol (Intermediate 7) are dissolved in dichloromethane (400 ml), Triethylamine (20 ml) and 4-dimethylamino-pyridine (400 mg) are added and the mixture is stirred at 0° C. for 2 hours and kept at 5° C. for 12 hours. Dichloromethane (800 ml) is added and the solution is washed with saturated aqueous sodium hydrogen carbonate solution (3×200 ml). The organic solution is then washed with water (2×200 ml), dried with sodium sulfate and evaporated to 200 ml. The solution is filtered through a plug of silica gel and evaporated. The title compound is isolated by crystallization from ethyl acetate.

2-Palmitoyl-1,3-benzylidene glycerol (Intermediate 9)

2-Nosyl-1,3-benzylidene glycerol (Intermediate 8) (2 g, 1 ekv) is dissolved in dimethylformamide (100 ml). The cesium salt of palmitinic acid (1 ekv) (prepared from palmitinic acid and cesium carbonate) is added, and the reaction mixture is stirred at ambient temperature for 12 hours. The mixture is evaporated and the title compound is isolated after purification (silica column, ethyl acetate and hexane).

2-(c9,t11-octadecadienoyl)-1,3-benzylidene glycerol (Intermediate 10)

The title compound is prepared as Intermediate 9 using c9,t11-octadecadienoic acid cesium salt (prepared from the acid and cesium carbonate).

2-(t10,c12-octadecadienoyl)-1,3-benzylidene glycerol (Intermediate 11)

The title compound is prepared as Intermediate 10 using t10,c12-octadecadienoic acid cesium salt (prepared from the corresponding acid and cesium carbonate).

2-Palmitoyl-1,3-glycerol (Intermediate 12)

The title compound is prepared by hydrolysis of 2-palmitoyl-1,3-benzylidene glycerol (Intermediate 9). 2-Palmitoyl-1,3-benzylidene glycerol (2 g, 1 ekv) and boronic acid (0,56, 2 ekv) are suspended in triethylborate (20 ml). The mixture is stirred at ambient temperature until the solution is clear. The mixture is evaporated. The crude product is dissolved in diethyl ether (100 ml) and washed with water (2×50 ml). The organic phase is dried with sodium sulfate and evaporated yielding the title compound.

2-(c9,t11-octadecadienoyl)-1,3 glycerol (Intermediate 13)

The title compound is prepared by hydrolysis of 2-c9,t11-octadecadienoyl-1,3-benzylidene glycerol (Intermediate 10) according to the method in Intermediate 12.

2-(t10,c12-octadecadienoyl)-1,3-glycerol (Intermediate 14)

The title compound is prepared by hydrolysis of 2-t10,c12-octadecadienoyl-1,3-benzylidene glycerol (Intermediate 11) according to the method in Intermediate 12.

1,3-Ditosyl-2-palmitoyl-1,3-glycerol (Intermediate 15)

2-Palmitoyl-1,3-glycerol (Intermediate 12) (0.4 g, 1 ekv) is dissolved in pyridine (10 ml) p-Toluenesulphonyl chloride (0.5 g, 2.5 ekv) is gradually added. The mixture is stirred for 12 hours at ambient temperature, evaporated and the title compound is crystallized from ethanol.

1,3 -Ditosyl-2-(c9,t11-octadecadienoyl) glycerol (Intermediate 16)

The title compound is prepared similar to Intermediate 15 starting with Intermediate 12.

1,3-Ditosyl-2-(t10,c12-octadecadienoyl) glycerol (Intermediate 17)

The title compound is prepared similar to Intermediate 15 starting with Intermediate 14.

1,3-Dipalmitoyl-2-nosyl-glycerol (Intermediate 18)

1,3-palmitoyl glycerol (Intermediate 4) (2.5 g, 4.4 mmol) is dissolved in dichloromethane (60 ml), 4-nitrobenzenesulphonyl chloride (1.2 g, 5.5 mmol) 4-dimethylaminopyridine (25 mg, 0.2 mmol) and triethyl amine (1.12 g, 11 mmol) are added. The mixture is stirred for 3 days at 0° C., Dichloromethane (200 ml) is added and the organic solution is washed with saturated aqueous sodium hydrogen carbonate solution (2×200 ml) and then washed with water (2×200 ml). The organic phase is dried with sodium sulfate and evaporated. The title compound is purified by chromatography (silica, ethyl acetate and hexane).

1,3-di (c9,t11-octadecadienoyl)-2-nosyl glycerol (Intermediate 19)

The title compound is prepared similar to Intermediate 18 starting from Intermediate 5.

1,3-di(t10,c12-octadecadienoyl)-2-nosyl glycerol (Intermediate 20)

The title compound is prepared similar to Intermediate 18 starting from Intermediate 6.

EXAMPLE 9

1,3-di(c9,t11-octadecadienoyl)-2-palmitoyl glycerol (triglyceride)

1,3-Ditosyl-2-palmitoyl-1,3-glycerol (Intermediate 15) (1 ekv) and c9,t11-octadecadienoic acid cesium salt (2 ekv) are suspended in toluene and dimethylformamide (1:1). The mixture is stirred at ambient temperature for 12 hours. The solvents are removed by evaporation and the title compound is isolated after chromatography (silica, ethyl acetate and hexane).

EXAMPLE 10

1,3-di(t10,c12-octadecadienoyl)-2-palmitoyl glycerol (triglyceride)

The title compound is prepared similar to Example 9 starting with t10,c12-octadecadienoic acid cesium salt.

EXAMPLE 11

1,2,3-tri(c9,t11-octadecadienoyl)-glycerol (triglyceride)

The title compound is prepared similar to Example 9 starting with Intermediate 16 and c9,t11-octadecadienoic acid cesium salt. This compound can also be prepared directly from glycerol and activated acid derivative (acid chloride or acid anhydride) or by use of coupling agents like for example dicyclohexyl-carbodiimide (DCC).

EXAMPLE 12

1,3-di(t10,c12-octadecadienoyl-2-(c9,t11-octadecadienoyl)-glycerol (triglyceride)

The title compound is prepared similar to Example 9 starting with Intermediate 16 and t10,c12-octadecadienoic acid cesium salt.

EXAMPLE 13

1,3-Dipalmitoyl-2-(c9,t11-octadecadienoyl)-glycerol (triglyceride)

The title compound is prepared similar to Example 9 starting with Intermediate 16 and palmitoyl cesium salt.

EXAMPLE 14

1,2,3-tri(t10,c12-octadecadienoyl)-glycerol (triglyceride)

The title compound is prepared similar to Example 9 starting with Intermediate 17 and t10,c12-octadecadienoic acid cesium salt. This compound can also be prepared directly from glycerol and activated acid.

EXAMPLE 15

1,3-di(c9,t11-octadecadienoyl)-2-(t10,c12-octadecadienoyl)-glycerol (triglyceride)

The title compound is prepared similar to Example 9 from Intermediate 17 and c9,t11-octadecadienoid acid cesium salt.

EXAMPLE 16

1,3-dipalmitoyl-2-(t10,c12-octadecadienoyl)-glycerol (triglyceride)

The title compound is prepared similar to Example 9 from Intermediate 17 and palmitoyl cesium salt.

EXAMPLE 17

1,3-Diplamitoyl-2-(c9,t11-octadecadienoyl)-glycerol (triglyceride)

Same compound as in Example 13, but different method. 1,3-Dipalmitoyl-2-nosyl glycerol (Intermediate 18) (0.25 g, 0.3 mmol) is dissolved in dimethylformamide (5 ml). c9,t11-Octadecadineoic acid cesium salt (1 ekv) is added and the mixture is stirred for 48 hours at ambient temperature. Dichloromethane (50 ml) is added and the mixture is washed with saturated aqueous sodium hydrogen carbonate solution (2×30 ml). The organic phase is dried ($Na_2SO_4$) and evaporated—The title compound is isolated after chromatography (silica, ethyl acetate and hexane).

EXAMPLE 18

1,3-Dipalmitoyl-2-(t10,c12-octadecadienoyl)-glycerol (triglyceride)

This compound is the same as in Example 16, but different method. The title compound is prepared similar to Example 20 starting from Intermediate 18 and t10,c12-octadecadienoic acid cesium salt.

EXAMPLE 19

1,2,3-tri(c9,t11-octadecadienoyl)-glycerol (triglyceride)

Same compound as Example 11, but different method. This compound is prepared similar to Example 20 starting from Intermediate 19 and c9,t11-octadecanoic acid cesium salt.

EXAMPLE 20

1,3-di(t10,c12-octadecadienoyl)-2-palmitoyl glycerol (triglyceride)

Same compound as Example 10, but different method. This compound is prepared similar to Example 17 starting from Intermediate 20 and palmitic acid cesium salt.

In these examples, palmitic acid has been utilized as a representative non-CLA fatty acid. Similar triglycerides can be prepared from other fatty acids including both saturated, unsaturated and poly-unsaturated fatty acids. CLA triglycerides conjugates can also be prepared with biologically active acids or drugs. Additionally, mixtures of CLAs can be used to prepare mixtures of triglycerides.

What should be clear from above is that the present invention provides novel acylglycerides comprising CLA and at least one other fatty acyl residue (e.g., ω3, ω6, and ω9 fatty acyl residues) which can be used in pharmaceutical compositions, animal feeds and in products suitable for human consumption. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

What is claimed is:

1. An acylglyceride having the following structure:

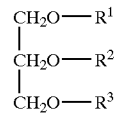

wherein R1 and R3 are acyl residues selected from the group consisting of 10,12; 9,11; 8,10; and 11,13 octadecadienoate and R2 is selected from the group consisting of medium chain fatty acyl residues.

2. The acylglyceride of claim 1, wherein said medium chain fatty acyl residue is selected from the group consisting of acyl residues of the following acids: decanoic acid, undecanoic acid, 10-undecanoic acid, lauric acid, cis-5-dodecanoic acid tridecanoic acid, myristic acid, and myristoleic acid.

3. A powder comprising at least one type of acylglyceride as set forth in claim 1.

4. An oil comprising at least one type of acylglyceride as set forth in claim 1.

5. The oil of claim 4, wherein said oil further comprises an antioxidant.

6. A food composition comprising at least one type of acylglyceride as set forth in claim 1.

7. The food composition of claim 6, wherein said food composition is a functional food, nutritional supplement food, infant food, pregnancy food, or elderly food.

8. A pharmaceutical composition comprising at least one type of glyceride as set forth in claim 1.

9. A nutritional or pharmaceutical composition comprising at least one type of acylglyceride as set forth in claim 1 and a carrier suitable for oral, intraintestinal, or parenteral administration.

* * * * *